United States Patent [19]

Wagner et al.

[11] Patent Number: 4,537,753
[45] Date of Patent: Aug. 27, 1985

[54] REMOVAL OF $CO_2$ AND $H_2S$ FROM NATURAL GASES

[75] Inventors: Eckhart Wagner, Ludwigshafen; Klaus Volkamer, Frankenthal; Ulrich Wagner, Limburgerhof, all of Fed. Rep. of Germany

[73] Assignee: BASF Aktiengesellschaft, Fed. Rep. of Germany

[21] Appl. No.: 537,837

[22] Filed: Sep. 30, 1983

[30] Foreign Application Priority Data

Oct. 2, 1982 [DE] Fed. Rep. of Germany ....... 3236600

[51] Int. Cl.$^3$ .............................................. B01D 53/34
[52] U.S. Cl. ...................... 423/228; 423/229
[58] Field of Search ................ 423/220, 228, 229

[56] References Cited

U.S. PATENT DOCUMENTS

| | | | |
|---|---|---|---|
| 2,477,314 | 7/1949 | Scharmann | 423/220 |
| 2,860,030 | 11/1958 | Goldtrap et al. | 423/229 X |
| 3,622,267 | 11/1971 | Bartholome et al. | 423/229 |
| 4,336,233 | 6/1982 | Appl et al. | 423/228 |

*Primary Examiner*—Earl C. Thomas
*Attorney, Agent, or Firm*—Keil & Weinkauf

[57] ABSTRACT

$CO_2$ and, where relevant, $H_2S$ are removed from natural gases which contain $CO_2$ and may or may not contain $H_2S$ by a process in which the said natural gases are treated, in an absorption stage at from 40° to 100° C., with an aqueous absorption liquid containing from 20 to 70% by weight of methyldiethanolamine, the treated natural gases are taken off at the top of the absorption stage, the aqueous absorption liquid laden with $CO_2$ and, where relevant, $H_2S$ is taken off at the bottom of the absorption stage and then regenerated in one or more flash stages, and the regenerated absorption liquid is recycled to the absorption stage.

5 Claims, 1 Drawing Figure

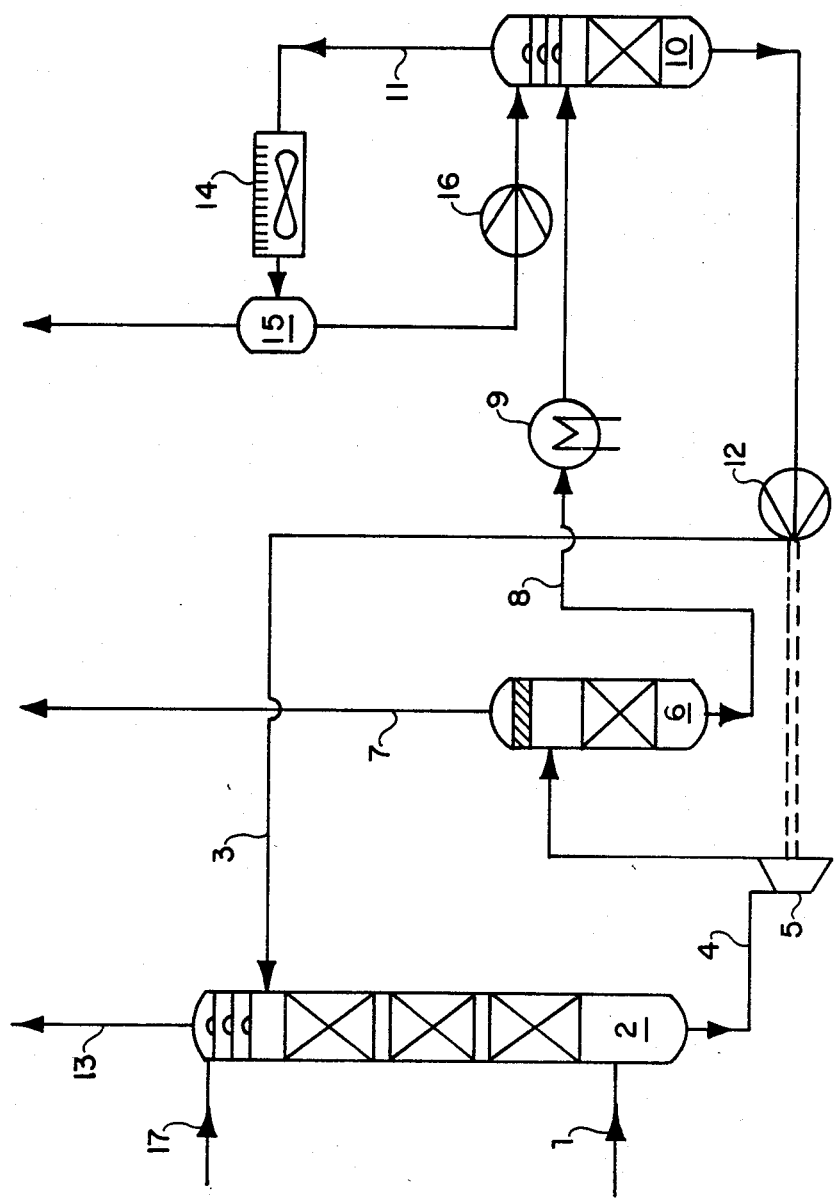

REMOVAL OF CO₂ AND H₂S FROM NATURAL GASES

The present invention relates to a process for the removal of $CO_2$ and, where relevant, $H_2S$ from natural gases by means of an aqueous absorption liquid.

It has been disclosed, for example, in A. L. Kohl-F. C. Riesenfeld, Gas Purification, 3rd Edition, 1979, that aqueous solutions of monoethanolamine or diethanolamine or a mixture of cyclotetramethylenesulfone and an aqueous solution of diisopropanolamine can be used as solvents for removing $CO_2$ and, where relevant, $H_2S$ from natural gases. In these processes, it is necessary for the solvent which is laden with $CO_2$ and, where relevant, $H_2S$ to be regenerated in a stripping column by feeding in steam; this requires a substantial amount of energy. Where $CO_2$ and, where relevant, $H_2S$ are removed from natural gases containing higher hydrocarbons by means of a mixture of cyclotetramethylenesulfone and an aqueous solution of diisopropanolamine, an additional disadvantage is that the higher hydrocarbons have a relatively high solubility in this solvent, so that the acid gas taken off at the top of the stripping column has a relatively high hydrocarbon content which, if the acid gas contains $H_2S$, can lead to difficulties in a downstream Claus unit. Furthermore, primary or secondary alkanolamines, eg. monoethanolamine or diethanolamine, can only be used in the form of relatively dilute aqueous solutions since higher concentrations can cause severe damage to plant components as a result of corrosion.

There has therefore been a need for a process for removing $CO_2$ and, where relevant, $H_2S$ from natural gases, by means of which the disadvantages of the conventional processes can be avoided.

It is an object of the present invention to provide a process for removing $CO_2$ and, where relevant, $H_2S$ from natural gases which contain $CO_2$ and may or may not contain $H_2S$, which requires a small amount of energy for its operation and in which the loss of higher hydrocarbons can be kept low.

We have found that this and other objects and advantages are achieved, in accordance with this invention, by a process for removing $CO_2$ and, where relevant, $H_2S$ from natural gases which contain $CO_2$ and may or may not contain $H_2S$, wherein the said natural gas is treated, in an absorption stage at from 40° to 100° C., with an aqueous absorption liquid containing from 20 to 70% by weight of methyldiethanolamine, the treated natural gas is taken off at the top of the absorption stage, the aqueous absorption liquid laden with $CO_2$ and, where relevant, $H_2S$ is taken off at the bottom of the absorption stage, and then regenerated in one or more flash stages, and the regenerated absorption liquid is recycled to the absorption stage.

In the novel process, the solvent laden with $CO_2$ and, where relevant, $H_2S$ is regenerated without the use of a stripping column, simply by flashing in one or more flash stages. By dispensing with the stripping column and the steam feed for the stripping process, both capital costs and energy costs can be substantially reduced. Furthermore, in the novel process it is possible to use relatively high methyldiethanolamine concentrations in the absorption liquid without this entailing corrosion damage in the gas wash unit.

The novel process is advantageously used for removing $CO_2$ and, where relevant, $H_2S$ from natural gases which contain higher hydrocarbons in addition to methane. These higher hydrocarbons are in general $C_2$–$C_{30}$-hydrocarbons, preferably $C_2$–$C_{20}$-hydrocarbons, in particular $C_2$–$C_{12}$-hydrocarbons, which as a rule are aliphatic, eg. ethane, propane, isobutane, n-butane, isopentane, n-pentane, the hexanes, heptanes, octanes, nonanes and decanes and the higher homologs. The higher hydrocarbons can contain, in addition to the aliphatic hydrocarbons, aromatic hydrocarbons such as benzene. In general, the natural gases contain from 0.1 to 40, preferably from 0.5 to 30, in particular from 1 to 20, mole % of the higher hydrocarbons.

The natural gases contain in general from 1 to 90, preferably from 2 to 90, in particular from 5 to 60, mole % of $CO_2$, and can also contain $H_2S$ as a further acid gas, for example in an amount of from a few mole ppm, for example 1 mole ppm, to 50 mole %.

The solvent used for the novel process is an aqueous absorption liquid containing from 20 to 70, preferably from 30 to 65, in particular from 40 to 60, % by weight of methyldiethanolamine. Advantageously, an aqueous methyldiethanolamine solution is employed, for example an aqueous solution of technical-grade methyldiethanolamine. In an advantageous embodiment of the process, the aqueous methyldiethanolamine solution used additionally contains from 0.1 to 1, preferably from 0.2 to 0.8, in particular from 0.25 to 0.6, mole/liter of a secondary amine or alkanolamine, preferably methylmonoethanolamine, very particularly advantageously piperazine.

The novel process is carried out as follows: the natural gas containing the $CO_2$ and, where relevant, $H_2S$ is first treated, in an absorption stage, with the methyl-diethanolamine-containing absorption liquid at from 40° to 100° C., preferably from 50° to 90° C., in particular from 60° to 80° C. The pressure in the absorption stage is in general from 10 to 110, preferably from 20 to 100, in particular from 30 to 90, bar. The absorption stage is advantageously an absorption column, in general a packed column or a column equipped with trays. Advantageously, the natural gas to be treated is fed in at the bottom and the absorption liquid is fed in at the top of the absorption column, the acidic gases $CO_2$ and, where it is present in the natural gas, $H_2S$ being washed out by a counter-current procedure. While any $H_2S$ present is advantageously washed out to a substantial extent, in general so that the treated natural gas has an $H_2S$ content of not more than 120, preferably not more than 10, in particular not more than 3, mole ppm, it may be advantageous to wash out the $CO_2$ from the natural gas so that the treated natural gas contains not more than about 0.5–6, preferably from 0.5 to 5, in particular from 1 to 4, mole % of $CO_2$. The treated natural gas is advantageously taken off at the top of the absorption stage, expediently at a point above the feed of the absorption liquid. The absorption liquid laden with the acid gases $CO_2$ and, where relevant, $H_2S$ is advantageously taken off at the bottom of the absorption zone.

The laden absorption liquid is then regenerated in one or more flash stages. In the last flash stage, or in the single flash stage where only one such stage is employed, the pressure is advantageously let down to about 1–3, preferably from 1 to 1.8, in particular from 1 to 1.5, bar. It may also be advantageous to operate the last flash stage or the single flash stage under reduced pressure, for example under from 0.5 to about 1, preferably from 0.8 to about 1, bar. It can be advantageous to use two or more, for example from 2 to 5, preferably 2 or 3, in particular 2, flash stages for the regeneration of the laden absorption liquid. Preferably, the pressure of the latter is let down to not less than 5 bar in the first flash stage after the absorption stage. It can be advantageous if the pressure to which the absorption liquid is let down in this first flash stage is furthermore not less than the partial pressure of $CO_2$, or the sum of the partial pressures of $CO_2$ and $H_2S$, in the natural gas fed into the absorption stage and containing $CO_2$ and, where relevant, $H_2S$. In this procedure, the evaporation of water and the associated energy losses as well as the losses of hydrocarbons can be kept particularly low. Flashing is advantageously carried using flash vessels which can, for example, also be in the form of columns. These flash vessels need not contain special baffles. However, it is also possible to use packed columns or columns equipped with replaceable trays.

As a rule, heat is supplied to the process to compensate for heat losses due to the process, for example those resulting from the flash. This is advantageously done in a heat exchange zone which is located upstream from the last flash stage, or from the single flash stage where only one such stage is used, and in which the laden absorption liquid is heated before flashing in the last or single flash stage. As a rule, the absorption liquid is heated by not more than 20° C. in the exchange zone, reaching a temperature of in general not more than 90° C., as a rule not more than 85° C. In general heat exchangers, eg. a tubular heat exchanger, are used for the heat exchange zone.

The acid gases $CO_2$ and, where relevant, $H_2S$ are advantageously taken off at the top of the last flash stage. Where the acid gas removed contains $H_2S$, it is advantageously worked up by oxidizing the $H_2S$, for example in a Claus unit. The regenerated absorption liquid taken off at the bottom of the last flash stage is recycled to the absorption zone.

The example which follows illustrates the invention in more detail, the course of the process being shown diagrammatically in the Figure.

A natural gas which contains $CO_2$ and may or may not contain $H_2S$ and higher hydrocarbons, eg. aliphatic $C_2$–$C_{10}$-hydrocarbons, is passed under superatmospheric pressure, via line 1, into the bottom of absorption column 2. At the same time, an absorption liquid comprising from 20 to 70% strength by weight aqueous methyldiethanolamine solution is passed via line 3 to the top of the absorption column. The absorption liquid, which is fed counter-current to the natural gas, becomes laden with the acid gases $CO_2$ and, where this is present in the natural gas to be washed, $H_2S$, and the laden absorption liquid is taken off at the bottom of the absorption column via line 4. The washed natural gas is taken off at the top of the absorption column via line 13. The stream of laden absorption liquid 4 is then let down to not less than 5 bar in a flash chamber 6, for example via a valve or, preferably, an expansion turbine 5. In this stage, an intermediate flash gas containing hydrocarbons and $CO_2$ is liberated from the absorption liquid and is taken off at the top of flash chamber 6 via line 7. At the bottom of flash chamber 6, the absorption liquid which has been partially let down is taken off via line 8 and heated in heat exchanger 9, for example by 1° to 15° C., and the heated absorption liquid is let down, for example to 1-2 bar, in a second flash chamber 10. This liberates a $CO_2$-rich flash gas, for example having a $CO_2$ concentration of 98 mole %, and this gas is taken off at the top of flash chamber 10 via line 11. The regenerated absorption liquid taken off at the bottom of flash chamber 10 is recycled to the top of absorption column 2 with the aid of a circulatory pump 12. Advantageously, the gas taken off via line 11 is cooled in heat exchanger 14 in order to condense steam liberated by flashing. The water separated out in separating vessel 15 during this procedure is recycled to the top of flash chamber 10 via pump 16. In general, water is fed to the top of absorption column 2 via line 17, so that the loss of methyldiethanolamine can be kept low by means of a water wash.

The Example which follows illustrates the invention.

EXAMPLE

In an absorption column, 3.15 kmol/hour of a $CO_2$-containing natural gas are washed, under 75 bar, with a 50% strength by weight aqueous methyldiethanolamine solution as the absorption liquid. The gas to be treated has the following composition:

$CO_2$: 10.0 mole %;
$CH_4$: 75.0 mole %;
higher hydrocarbons
($C_2$–$C_{12}$-hydrocarbons): 15.0 mole %.

The temperature of the absorption liquid in the feed to the absorption column is 70° C. The $CO_2$ content in the washed gas is 2.0 mole %. The laden washing agent which leaves the absorption column is let down to 20 bar in a first flash chamber. In this procedure, 0.04 kmol/liter of a hydrocarbon-rich intermediate flash gas having a $CO_2$ concentration of 34.3 mole % is liberated from the solution and is taken off at the top of the first flash chamber. The partially let down absorption liquid is then heated by about 5° C. in a heat exchanger. The heated absorption liquid is let down to 1.3 bar in a second flash chamber. In this procedure 0.241 kmol/hour of a $CO_2$-rich flash gas having a $CO_2$ concentration of 97.55 mole %, a methane concentration of 1.68 mole % and a concentration of higher hydrocarbons of 0.77 mole % is liberated and is taken off at the top of the second flash chamber. The absorption liquid taken off at the bottom of the flash chamber is recycled to the top of the absorption column with the aid of a circulatory pump.

In a comparative example, the above experiment is repeated under the same conditions but using a 30% strength by weight aqueous monoethanolamine solution. When the solvent is heated to the same extent as the aqueous methyldiethanolamine solution, the $CO_2$ concentration of the washed gas can be reduced merely to 7 mole %.

We claim:

1. A process for removing $CO_2$ and, where relevant, $H_2S$ from a natural gas which contains $CO_2$ and may or may not contain $H_2S$, which comprises:
   (a) treating said natural gas in an absorption stage at from 40° to 100° C. and at a pressure of from 10 to 110 bar with an aqueous absorption liquid containing from 20 to 70% by weight of methyldiethanolamine by feeding in the natural gas at the bottom and the aqueous absorption liquid at the top of the absorption stage, $CO_2$ and, where it is present, $H_2S$ being washed out by a counter-current procedure;
   (b) taking off the treated natural gas at the top of the absorption stage;
   (c) taking off the aqueous absorption liquid laden with $CO_2$ and, where relevant, $H_2S$ at the bottom of the absorption stage;

(d) regenerating the laden aqueous absorption liquid without the use of a stripping column by flashing the liquid in one or more flash stages, letting down the pressure in the last flash stage, or in the single flash stage where only one such stage is employed, to about 1 to 3 bar; and (e) recycling the regenerated absorption liquid to the absorption stage.

2. The process of claim 1, wherein $CO_2$ and, where relevant, $H_2S$ are removed from a natural gas containing higher hydrocarbons in addition to methane.

3. The process of claim 1, wherein two or more flash stages are used for regenerating the laden absorption agent, and the pressure of the latter is let down to not less than 5 bar in the first flash stage after the absorption stage.

4. The process of claim 1, wherein the absorption liquid contains from 30 to 65% by weight of methyldiethanolamine.

5. The process of claim 1, wherein the absorption liquid contains from 40 to 60% by weight of methyldiethanolamine.

* * * * *